(12) United States Patent
Arnone et al.

(10) Patent No.: US 7,244,934 B2
(45) Date of Patent: Jul. 17, 2007

(54) ANALYSIS APPARATUS AND METHOD

(75) Inventors: Donald Dominic Arnone, Cambridge (GB); Philip Francis Taday, Cambridge (GB)

(73) Assignee: TeraView Limited (GB)

( * ) Notice: Subject to any disclaimer, the term of this patent is extended or adjusted under 35 U.S.C. 154(b) by 0 days.

(21) Appl. No.: 10/504,719

(22) PCT Filed: Feb. 14, 2003

(86) PCT No.: PCT/GB03/00660

§ 371 (c)(1),
(2), (4) Date: Mar. 14, 2005

(87) PCT Pub. No.: WO03/069318

PCT Pub. Date: Aug. 21, 2003

(65) Prior Publication Data

US 2005/0156120 A1     Jul. 21, 2005

(30) Foreign Application Priority Data

Feb. 15, 2002   (GB) ................................. 0203698.6

(51) Int. Cl.
*G01N 21/49* (2006.01)
(52) U.S. Cl. .................. 250/336.1; 250/358.1
(58) Field of Classification Search ............. 250/336.1, 250/358.1
See application file for complete search history.

(56) References Cited

U.S. PATENT DOCUMENTS

| | | | |
|---|---|---|---|
| 2,792,548 A | 5/1957 | Hershberger | |
| 3,932,180 A * | 1/1976 | Griffiths et al. | 430/128 |
| 4,320,118 A * | 3/1982 | White et al. | 514/14 |
| 5,507,173 A | 4/1996 | Shearer et al. | |
| 5,710,430 A | 1/1998 | Nuss | 250/358.1 |
| 5,789,750 A * | 8/1998 | Nuss | 250/338.1 |
| 5,939,721 A * | 8/1999 | Jacobsen et al. | 250/330 |
| 6,844,552 B2 * | 1/2005 | Zhang et al. | 250/338.1 |
| 6,849,852 B2 * | 2/2005 | Williamson | 250/341.6 |
| 2001/0029436 A1 | 10/2001 | Fukasawa | |
| 2003/0113802 A1* | 6/2003 | Matzger et al. | 435/7.1 |

FOREIGN PATENT DOCUMENTS

| | | |
|---|---|---|
| GB | 2 347 835 | 9/2000 |
| GB | 2 360 186 | 9/2001 |
| GB | 2 360 842 | 10/2001 |
| WO | WO 00/75641 | 12/2000 |
| WO | WO 01/48457 | 7/2001 |

OTHER PUBLICATIONS

International Search Report dated Aug. 7, 2003.

* cited by examiner

*Primary Examiner*—Albert Gagliardi
(74) *Attorney, Agent, or Firm*—Ostrolenk, Faber, Gerb & Soffen, LLP

(57) ABSTRACT

A method for investigating the macromolecular structure of a molecular sample, the method composing irradiating the sample with radiation having a plurality of frequencies in the range of 25 GHz to 20 THz; detecting radiation reflected from and/or transmitted by said sample to obtain a spectra of the sample; and identifying structure in the resultant spectra which arises from intermolecular interactions.

42 Claims, 14 Drawing Sheets

ANALYSIS APPARATUS AND METHOD

The present invention relates generally to the field of apparatus and methods for obtaining information about the macro structure of a sample and particularly a molecular sample. More specifically, the present invention relates to obtaining information about the polymorphs of a molecular sample using radiation in the range from 25 GHz to 20 THz.

Many elements and molecules are capable of exhibiting at least one crystallographic arrangement when in the solid state. These different crystallographic arrangements are referred to as polymorphs or allotropes. A classic example of two polymorphs or allotropes is that of graphite and diamond which are both allotropes/polymorphs of carbon. Graphite and carbon have different mechanical, electrical and chemical properties and are easily distinguishable from their physical appearances.

However, many polymorphs exist which also have different chemical or other properties, but which are not so easily distinguished. Such polymorphs are of particular concern in the pharmaceutical fields where the chemical properties of one polymorph are well understood and whereas the chemical properties of the other polymorphs of the same molecule are either not understood or known to be disadvantageous. Thus, it is important to be able to accurately identify a particular polymorph of a molecule.

Further, as some molecules undergo phase changes to a different polymorphic state or pseudopolymorphic state, over time or due to pressure, temperature, radiation etc, it is also necessary to have a reliable and relatively quick method for establishing that the polymorphic structure of a sample has not changed during storage or transportation. A pseudopolymorphic form is a crystalline form containing solvent molecules such as ethanol or isopropanol.

Previously, X-ray diffraction spectroscopy has been used to distinguish between different polymorphs. This method has its drawbacks in that, ideally, large single crystals are required and the use of ionising radiation (X-rays) means that extra safety measures are required. Further, this method must be performed under vacuum.

Fourier transform-infrared spectroscopy (FTIR) in the mid infra-red range (900–3000 cm$^{-1}$) may also be used to obtain information about the crystallographic structure of a molecule. This technique probes the intra-molecular structure i.e. the nature of the bonds which form the individual molecules. The natural vibrational frequencies of the intramolecular bonds are affected by molecular interactions. Thus, a vibrational frequency for a particular intra-molecular bond may be shifted in frequency between different polymorphs. It is difficult to accurately interpret the results from this technique since small peak shifts are hard to measure and may arise due to other factors such as water absorption by the molecule.

Diffuse reflectance infra-red fourier transform spectroscopy can also be used but this is limited to the mid infra-red part of the spectrum. This technique provides good information about the structure of the molecule itself but is hard to interpret for information about the macromolecular structure.

Raman spectroscopy may also be used to study molecular vibrations close to the laser exciting line. However, the Raman scattering process is relatively inefficient and this results in long data acquisition times. The selection rules which control both Raman and infra-red absorption are different and thus different spectral information about the molecule is obtained from both of these techniques.

Solid state nuclear magnetic resistance (NMR) has also been used. However, currently, the technique is suffering from large errors when applied to solid state samples. Other non spectroscopic techniques have also been suggested such as scanning electron microscopy and light microscopy.

The above problems are at least partially addressed by the present invention which uses radiation in the so-called THz regime in order to probe the intermolecular bonds as opposed to the intramolecular bonds.

Thus, in a first aspect, the present invention provides method for investigating the macro structure of a sample, the method comprising irradiating the sample with radiation having a plurality of frequencies in the range from 25 GHz to 20 THz; detecting radiation reflected from and/or transmitted by said sample to obtain a spectra of the sample; and identifying structure in the resultant spectra which arises from intermolecular interactions in the sample.

The term macrostructure is used to refer to the amorphous or crystallographic structure of a solid or liquid sample. A liquid sample will often have some crystallographic structure, especially if the liquid sample is a saturated solution or a solution which is close to saturation.

Using radiation in the above frequency range, intermolecular vibrations are excited. The above frequency range is colloquially referred to as the THz frequency range. Preferably, the frequency range from 50 GHz to 15 THz is used, more preferably 100 GHz to 12 THz, even more preferably 0.5 THz to 10 THz.

Typically, the structure in the resultant spectra will manifest itself as peaks and/or troughs in the spectra. The user of the above method can then identify this structure in the spectra in order to determine information about the macrostructure of the sample.

The above method has many applications. For example, the method may be used for analysing new pharmaceuticals to establish the exact polymorph of a synthesised preparation. The exact structure of an unknown polymorph or pseudopolymorph may be determined by analysing each peak or trough of the resultant spectra which is believed to arise from an intermolecular bond.

The resultant spectra may also be compared with that obtained from a known polymorph in order to determine information about the sample. Thus, the method may be used to establish if a particular known polymorph has been obtained from a new or existing synthesis process. Hence, the method may be configured for use as a verification method for establishing if a desired polymorph has been correctly synthesised.

Some polymorphs are unstable and may revert to a different polymorph of the molecule if the storage temperature of the sample is changed, the storage pressure, storage illumination conditions are changed. Also, sometimes, the sample may change to a different polymorph over time in the absence of any change in the storage conditions of the sample. This causes serious problems during storage and transportation of pharmaceutical products.

The present invention may thus also be used as a monitoring method to verify the polymorphic or psuedopolymorphic structure of a molecule after or during storage or transportation.

The spectra of the sample may be obtained when the sample is located in a plastic bag or the like which will thus allow a sample to be monitored without the needed for the sample to be removed from hygienic packaging.

This allows the actual samples which will be sent to a client to be monitored as opposed to just performing a check of samples which have been stored under similar conditions.

The method of the present invention also allows a manufacturer to easily establish the optimum storage and transportation conditions for a sample.

In addition to determining information about the polymorphic structure of a sample, it is also useful to additionally obtain information about the intermolecular structure. Thus, preferably, the method further comprises irradiating the sample with radiation in the range of 25 THz to 120 THz and identifying structure in the resultant spectra which arises from intramolecular vibrations.

The above allows the method to establish both the inter and intramolecular structure of a sample. This is of particular use when the molecule may have isomers.

The absorption coefficient and/or the refractive index of the sample may be measured in order to obtain information about the sample.

The radiation may be pulsed or continuous wave radiation. Continuous wave radiation sometimes provides a cheaper alternative to pulsed radiation.

The incident radiation may be broad band radiation or it may comprise a plurality of discreet frequencies. The discrete frequencies may be chosen to coincide with expected structure in the resultant spectra of the sample.

The use of coherent radiation allows the power of the radiation to be kept low so as to avoid the sample heating. Preferably, the maximum power used is 2 $mW/cm^2$, more preferably 1.5 $mW/cm^2$, even more preferably about 1.3 $mW/cm^2$.

The sample may be cooled for analysis as this may enhance the efficiency of the source of the incident radiation or the detector. However, care must be taken to first establish that the sample does not undergo a polymorphic phase change when it is cooled for analysis. Thus, the sample may be held at a maximum temperature of up to 150K during irradiation, more preferably up to 10K.

Radiation in the claimed frequency range may be strongly absorbed by water which may affect the spectra for some samples. Thus, the sample is preferably irradiated under vacuum or in a dry atmosphere such a dry nitrogen or dry compressed air.

The sample may be irradiated using either transmission and/or reflection measurements. For transmission measurements, the sample is preferably, less than 5 mm, more preferably less than 2 mm, even more preferably less than 1 mm. The ability to perform transmission measurements on samples which are as thick as 5 mm, means that standard tablets which have a thickness of from 4 mm to 5 mm and generally about 4.5 mm can be analysed by the method.

The sample may be powderised prior to irradiation, The sample may then be compressed into a thin structure or may be sprayed onto a suitable supporting structure. The suitable supporting structure is preferably an inert material such as polyethylene.

The sample may also be powderised an mixed with an inert material such a polyethylene. Often, pharmaceuticals are supplied in tablet form where the actual ingredient is mixed with an inert filler material.

The spectra may be obtained by plotting the amplitude or a parameter related to the amplitude of the detection radiation in the time domain or frequency domain. The power of the detected radiation may also be plotted in the time or frequency domain.

More preferably, the absorption is plotted, this is calculated by plotting the log of the radiation detected from the sample divided by the radiation detected from a reference. The reference may be obtained by removing the sample from the apparatus and measuring the detected radiation, or it may be obtained from a suitable reference sample. For example, when the sample is of a mixture of an inert material and an active material, the reference sample may comprise the inert material.

It has been previously mentioned that the method is of particular use in determining the polymorphic structure of pharmaceuticals. Examples of pharmaceutical compounds which either exhibit or are expected to exhibit polymorphs are: AG-337, Ampicillin, Androstanolone, Aspartme, Benoxaprofen, Captopril, Carbamazepine anhydrate, Carbamazepine dihydrate, Carbovir, Cefaclor dihydrate, Cefamandole nafate, Cefazolin, Cefepime.2HCl, Chlorpropamide, Cimetidine, Compound H, Cortisone acetate, Cyclopenthiazide, Delavirdine mesylate, Diflunisal, 1,2-Dihydro-6-neopentyl-2-oxonicotinic, 11-α-Dimethyl-3-hydroxy-4-pyridone, Diphenhdramine HCl, Dirithromycin, Disodium clodronate, DuP 747, Erthtrocin, 13-Estradiol, Fluconazole, Flucinolone acetonide , p-Formyl-tiazs-cinnamic acid, Fosinopril sodium, Frusernide, Glburide, Glycine, Griseofulvin, Indomethacin, L-660,71, Lactose, Losartan, Lufenuron, Mefloquine HCl, 4'-Methyl-2'-nitroacetanilide, 5-Methyl-2-{(2-nitrophenyl)amino}-3-thiopheneccarbonitrile, MK-571, MK-679, Mofebutazone, Nabilione, Nedocromil magnesium, Neotame, Nicardipine HCl, Nimodipine, Oxyphenbutazone, Paracetamol, Paroxetine HCl, Phenylbutazone, Prednisolone teit.-butylacetate, Ranitidine HCl, RG-12525, Salbutamol, SC-25469, SC-41930, Spironolactone, SQ-33600, Sulfamethoxazole, Sulfaproxiline, Sulphanilainide and Testosterone.

In a second aspect, the present invention provides an apparatus for studying the macro structure of a molecular sample, the apparatus comprising:

an emitter for irradiating the sample with radiation having a plurality of frequencies in the range from 25 GHz to 20 THz;

a detector for detecting radiation reflected from and/or transmitted by the sample and producing a spectra of the sample;

means for identifying structure in the spectra arising from intermolecular vibrations.

Preferably, the means for identifying structure comprises comparing means to compare the detected spectra with known spectra. For example, the apparatus may comprise memory means which is preloaded with at least one spectra which is expected to at least closely correspond to the spectra of the sample. Alternatively, the memory means may be pre-loaded with a plurality of known spectra, the apparatus being configured to compare each of the spectra in the memory means with that of the sample.

The apparatus may be configured to monitor the quality of a batch of samples, the apparatus comprising comparing means to compare a resultant spectra with that of the established spectra of the batch of samples and alarm means which ermits an alarm signal when the spectra obtained from the sample differs from that of the established spectra.

The detector may be a direct detector of THz radiation or it may be of the type which converts THz radiation into an easily readable signal.

For example, the detector may comprise a non-linear crystal which is configured such that upon irradiation of a probe beam and a THz beam, the polarisation of the probe beam is rotated. The probe beam can be of a frequency which can be easily measured (for example near infra-red). Typical crystals which exhibit this effect, the so-called "AC Pockels" effect are GaAs, GaSe, $NH_4H_2PO_4$, ADP, $KH_2PO_4$, $KH_2ASO_4$, Quartz, $AlPO_4$, ZnO, CdS, GaP, $BaTiO_3$, $LiTaO_3$, $LiNbO_3$, Te, Se, ZnTe, ZnSe, Ba$_2$NaNb$_5$O$_{15}$, AgAsS$_3$, proustite, CdSe, CdGeAs$_2$, AgGaSe$_2$, AgSbS$_3$, ZnS, organic crystals such as DAST (4-N-methylstilbazolium. This type of detection mechanism is generally referred to as 'Electro-optic sampling' or EOS.

Alternatively, the detector could be a so-called photoconducting detector. Here, the detector comprises a photoconductive material such as low temperature grown GaAs, Arsenic implanted GaAs or radiation damaged Si on Sapphire. A pair of electrodes, for example in a bow-tie configuration or in a transmission line configuration are provided on a surface of the photoconductive material. When the photoconductive material is irradiated by the reflected radiation and also, the probe beam, a current is generated between the two electrodes. The magnitude of this photovoltage current is an indication of the magnitude of the THz signal.

Although it is possible to generate THz radiation directly, the most effective THz generation can be achieved by converting a pump beam into a THz beam. To do this, the source comprises a frequency conversion member and a source of a pump beam.

The pump beam may be supplied by a Ti:sapphire Yb:Er doped fibre, Cr:LiSAF, Yb:silica, Nd:YLF, Nd:Glass, Nd:YAG or Alexandrite laser There are many possible options for the frequency conversion member. For example, the frequency conversion member may comprise a non-linear member, which is configured to emit a beam of emitted radiation in response to irradiation by a pump beam. Preferably, the pump beam comprises at least two frequency components, (or two pump beams having different frequencies are used), the non-linear member can be configured to emit an emitted beam having a frequency which is the difference of the at least two frequencies of the pump beam or beams. Typical non-linear members are: GaAs or Si based semiconductors. More preferably, a crystalline structure is used. The following are further examples of possible materials:

NH$_4$H$_2$PO$_4$, ADP, KH$_2$PO$_4$, KH$_2$ASO$_4$, Quartz, AlPO$_4$, ZnO, CdS, GaP, BaTiO$_3$, LiTaO$_3$, LiNbO$_3$, Te, Se, ZnTe, ZnSe, Ba$_2$NaNb$_5$O$_{15}$, AgAsS$_3$, proustite, CdSe, CdGeAs$_2$, AgGaSe$_2$, AgSbS$_3$, ZnS, GaSe or organic crystals such as DAST (4-N-methylstilbazolium).

In order to produce an emitted beam having a frequency in the THz regime, preferably the at least two frequencies of the pump beam or beams are in the near infra-red regime. Typically, frequencies between $0.1 \times 10^{12}$ Hz and $5 \times 10^{14}$ Hz are used.

Alternatively the frequency conversion member is a photoconducting emitter, such an emitter comprises a photoconductive material such as low temperature grown or arsenic implanted GaAs or radiation damaged Si or Sapphire.

Electrodes which may be of any shape such as a dipole arrangement, a double dipole arrangement, a bow-tie arrangement or transmission line arrangement are provided on the surface of the photoconductive material. At least two electrodes are provided. Upon application of a bias between the electrodes and irradiation of a pump beam(s) having at least two different frequency components, a beam of radiation is emitted having a frequency different to that of the at least two frequency components of the pump beam or beams.

p-i-n emitters may also be used as the source. These are photodiodes which are irradiated with a short pulse laser (pulse length approximately 10 fs, wavelength approximately 800 nm). These emitters can emit at frequencies up to 20 THz.

When a pulse having a plurality of frequencies passes via a sample to a detector, the various frequencies will not arrive at the detector at the same time due to the frequency dependent response of the sample. A time domain signal can be established by measuring the amplitude of the detected radiation with respect to time. In order to achieve this, it is preferable if a scanning delay line is inserted into either the path of the probe or pump beam. The delay line can be configured to scan over the whole length of the pulse. This time domain spectra will be converted to a frequency domain spectra by fourier transforming the spectra The present invention will now be described with reference to the following preferred non-limiting embodiments in which:

Figure 11:
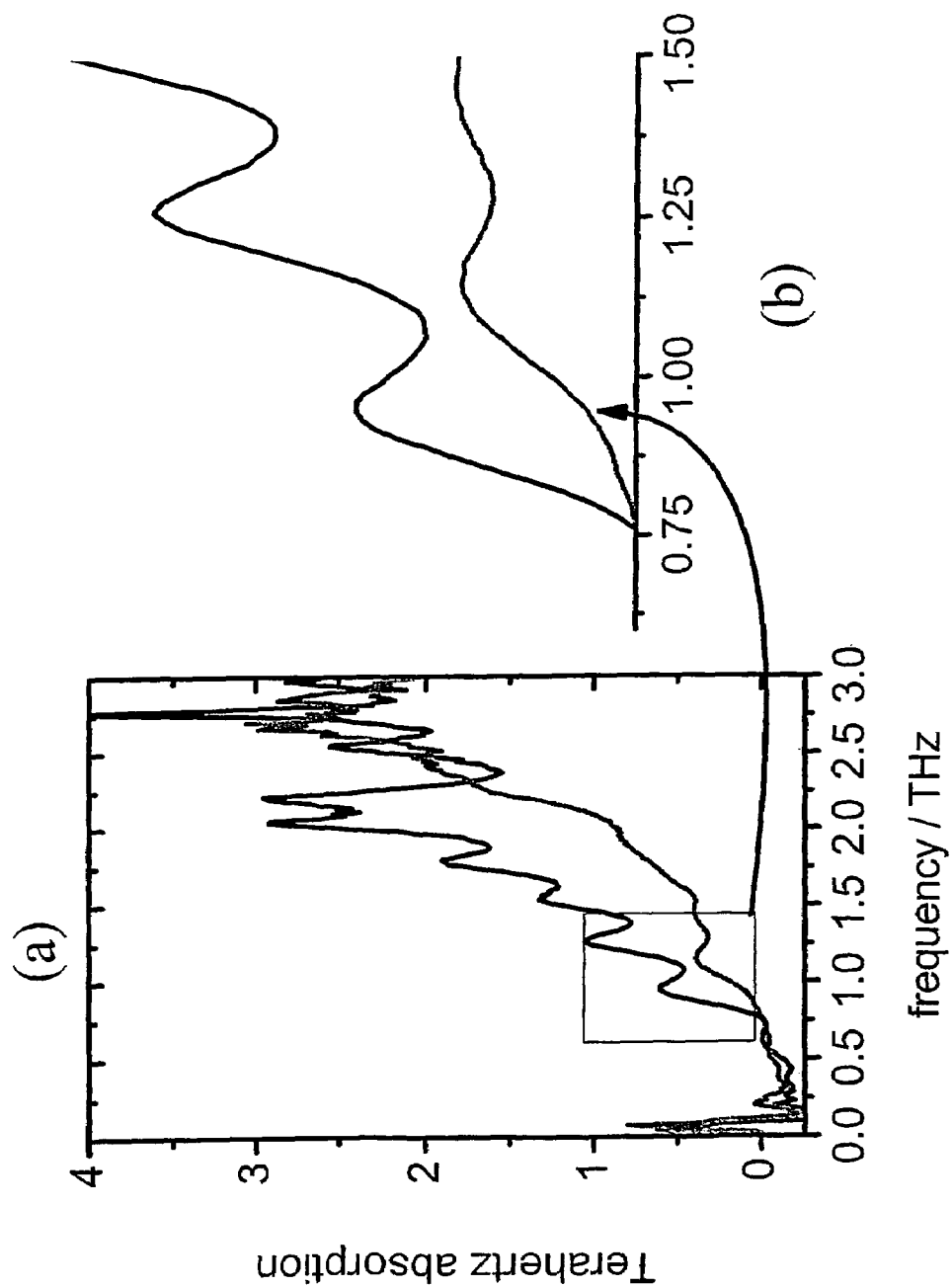
Figure 12:
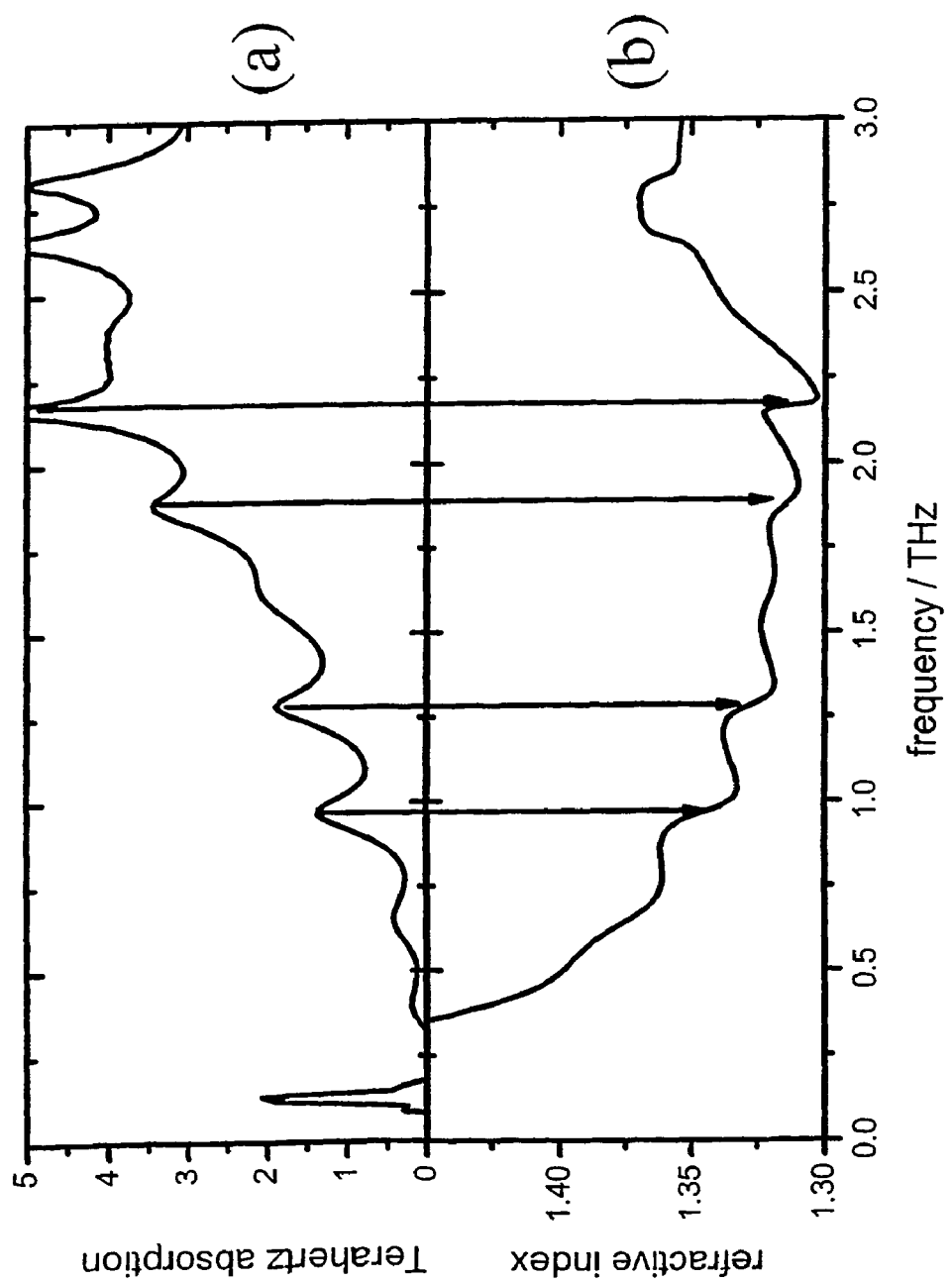
Figure 13:
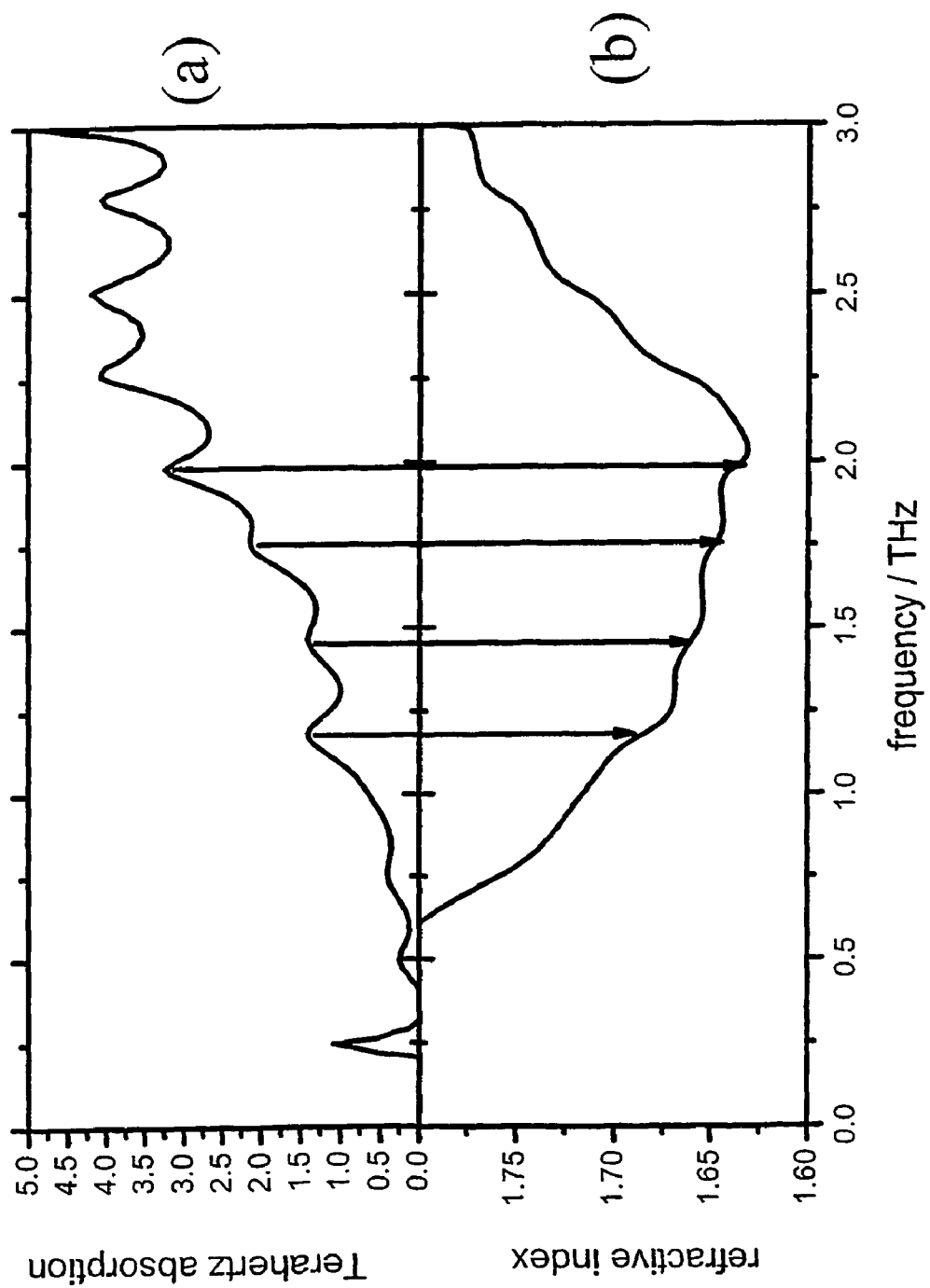
Figure 14:
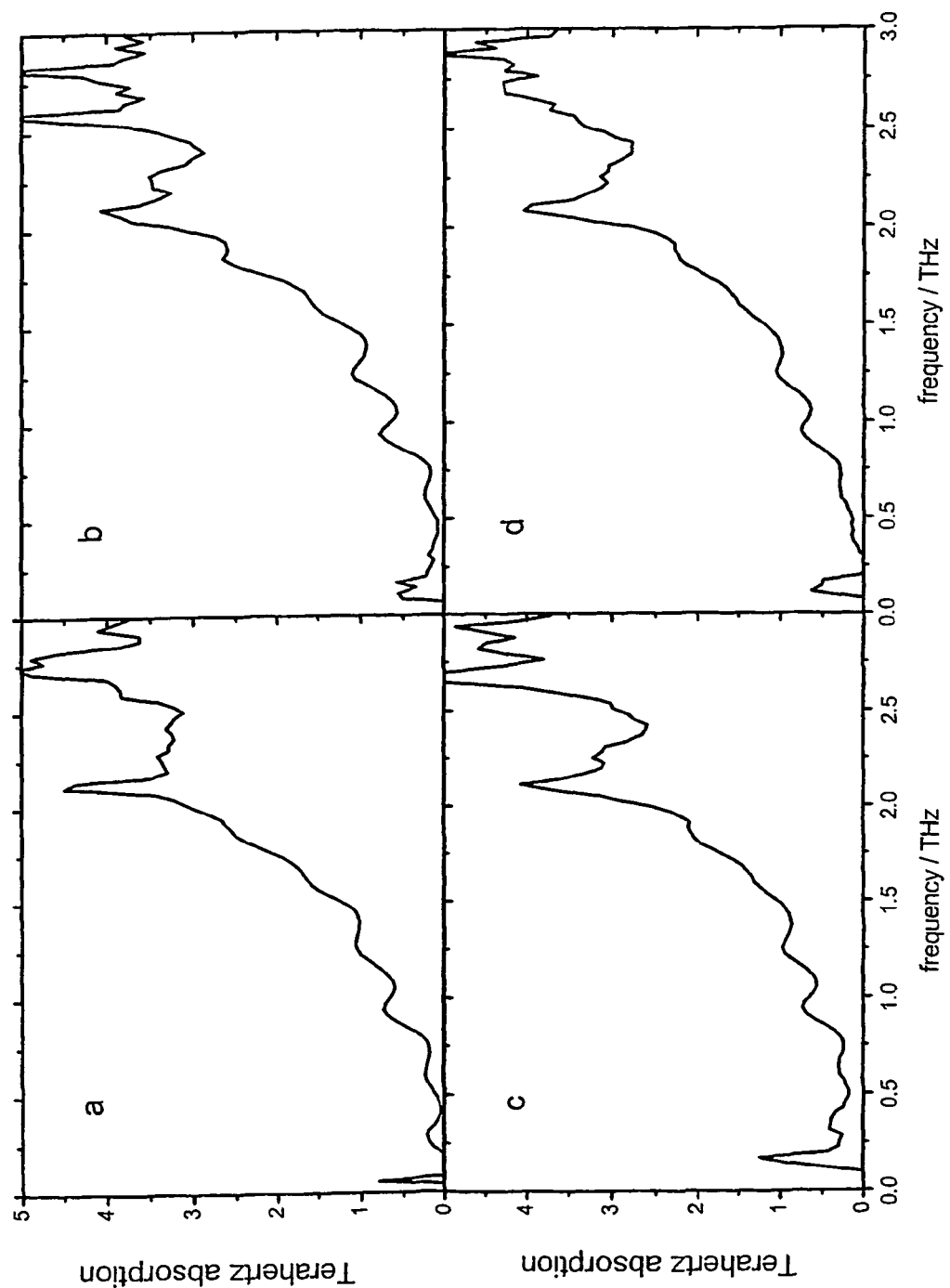

FIG. 11a is a plot of the THz absorption spectra for different samples of the first polymorph and second polymorph of ranitidine HCl described above with reference to FIGS. 5 and 6. The time domain waveform is plotted along the y axis and the frequency from 0 to 3 THz along the x axis. FIG. 11b is an enlarged version of the plot of FIG. 11a from 0.75 THz to 1.5 THz;

FIG. 12a is a plot of the THz absorption against frequency for the drug Apo-ranitidine (ApoTex). FIG. 12b is a plot of the refractive index against frequency for the drug Apo-ranitidine (ApoTex);

FIG. 13a is a plot of the THz absorption against frequency for the drug Zantac (Glaxo). FIG. 13b is a plot of the refractive index against frequency for the drug Zantac (Glaxo); and FIGS. 14a to d are plots of the THz absorption spectra against frequency for four ranitidine drug dosage tablets at room temperature from the following manufacturers (a) Eastern Pharmaceuticals Ltd., (b) Genelics UK Ltd,., (c) Tillomed and (d) Norton Ranbaxy Laboratories.

Figure 1:
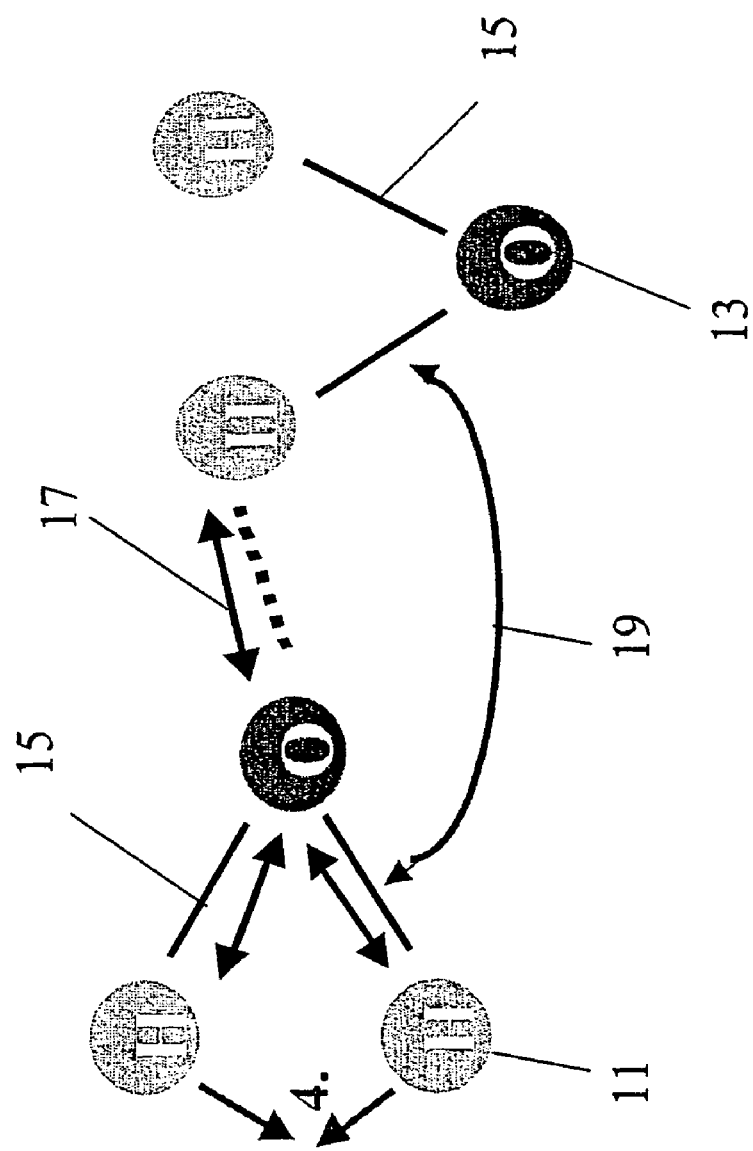
FIG. 1 is a schematic of two water molecules which are used to explain intra and inter molecular activity.

In FIG. 1, hydrogen bonding between a first water molecule 11 and a second water molecule 13 is shown. When the molecule is irradiated with radiation having frequencies which correspond to the resonant frequency of one or more of the intra 15 or inter 17 molecular bonds, these bonds start to vibrate and radiation having these resonant frequencies is absorbed by this radiation.

In FIG. 1, the intra molecular bonds 15 occur between the oxygen and hydrogen atoms of molecules 11 and 13. These bonds generally vibrate at frequencies within the mid infrared range.

Vibrations due to intermolecular interactions are shown as 17, this intermolecular bond is believed to be a hydrogen bond between the two molecules 11 and 13.

The formation of this hydrogen bond 17 between the two molecules 11, 13 will also affect the vibrational frequency of intramolecular bonds 15. This means that the absorption frequency of the intramolecular bond in an isolated molecular will be shifted slightly from that of the absorption frequency of an intramolecular bond in a water molecule which is hydrogen bonded to another molecule.

The present invention looks at the inter molecular reactions directly, i.e. the absorption due to hydrogen bond 17 in this situation.

Figure 2:
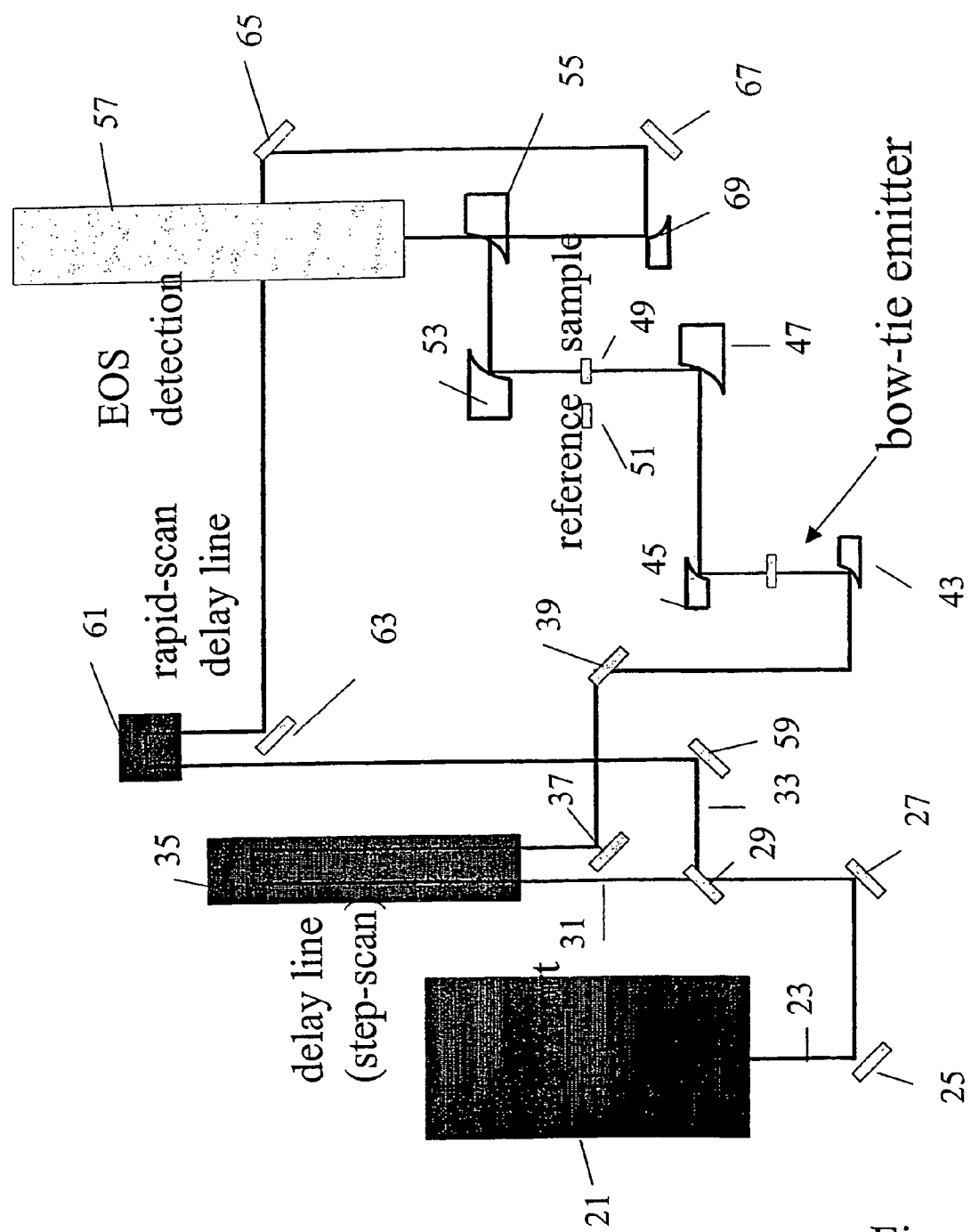
FIG. 2 illustrates a system which may be used for performing the method of the present invention.

FIG. 2 illustrates an apparatus which can be used to perform the method of the present invention.

The apparatus comprises an ultra-short pulse laser 21 which may be, for example, Ti:sapphire, Yb:Er doped fibre, Cr:LiSAF, Yb:silica, Nd:YLF, Nd:Glass, Nd:YAG or Alexandrite laser. This laser 21 emits pulses of radiation 23 each of which comprise a plurality of frequencies. This pulse is reflected by first mirror 25 and second mirror 27 into beam splitter 29. The beam splitter splits the beam into a pump pulse 31 which is used to irradiate the sample and a probe pulse 33 which is used during detection.

The pump pulse 31 is into first scanning delay line 35. Scanning delay line 37 in its simplest form comprises two mirrors which serve to reflect the beam through a 180°. These mirrors are then quickly swept backwards and forwards in order to vary the path length of the pump pulse 31. The output pump pulse from the first scanning delay line is then directed by mirrors 37 and into parabolic mirror 43.

Parabolic mirror 43 directs the pump pulse onto a source which comprises a frequency conversion member and a bow-tie emitter. The frequency conversion member is configured to mix the incident radiation and output radiation derived from the differences of the input frequencies, so-called difference frequency generation. This technique is described in more detail in GB 2 347 835.

The output is then reflected off second parabolic mirror 45 and onto third parabolic mirror 47 which directs the radiation onto sample 49. The sample may be replaced with a reference sample 51 in order to remove background features from the final results. The radiation which is transmitted through sample 49 is then collected by fourth parabolic mirror 53 and is then combined with the probe beam using combining parabolic mirror 55.

Combining parabolic mirror 55 comprises a parabolic surface with an aperture. The detected radiation is directly collected by parabolic surface, this is combined with the probe beam 33 which is transmitted through the aperture in the parabolic surface. The combined beams are then sent into an electro-optic sampling detection unit 57. The details of this are described in GB 2 347 835.

Prior to recombining with the pump beam 31, the probe beam 33 is directed by mirror 59 into second scanning delay line 61. This operates in the same manner as the first scanning delay line 35. The outputted probe beam 33 is then reflected off first probe beam 63 onto second probe beam mirror 65 and onto third probe beam mirror 67 into probe beam parabolic mirror 69. Parabolic mirror then directs the probe beam into the aperture of recombining parabolic mirror 55 for recombination with the pump beam.

The sample introduces a time delay in the path of the pump pulse. The delay is dependent on both the absorption coefficient and the refractive index of the sample. In order to obtain an EOS detection signal, the frequency component of the probe beam must be in phase with a frequency component of the pump beam. Variation of the first and second scanning delay line allows the phase of the probe beam and/or pump beam to be swept with respect to the pump beam and/or probe beam and thus allows for measurement of the delay time of each frequency component which passes through the sample.

In the apparatus of FIG. 2, the pump beam and probe beams are focussed using parabolic mirrors as opposed to glass lenses. This is because glass lenses disperse the pump beam, probe beam and the produced THz radiation. Thus, it is advantageous to design the system to avoid transmission of the radiation through anything other than the sample.

Figure 3:
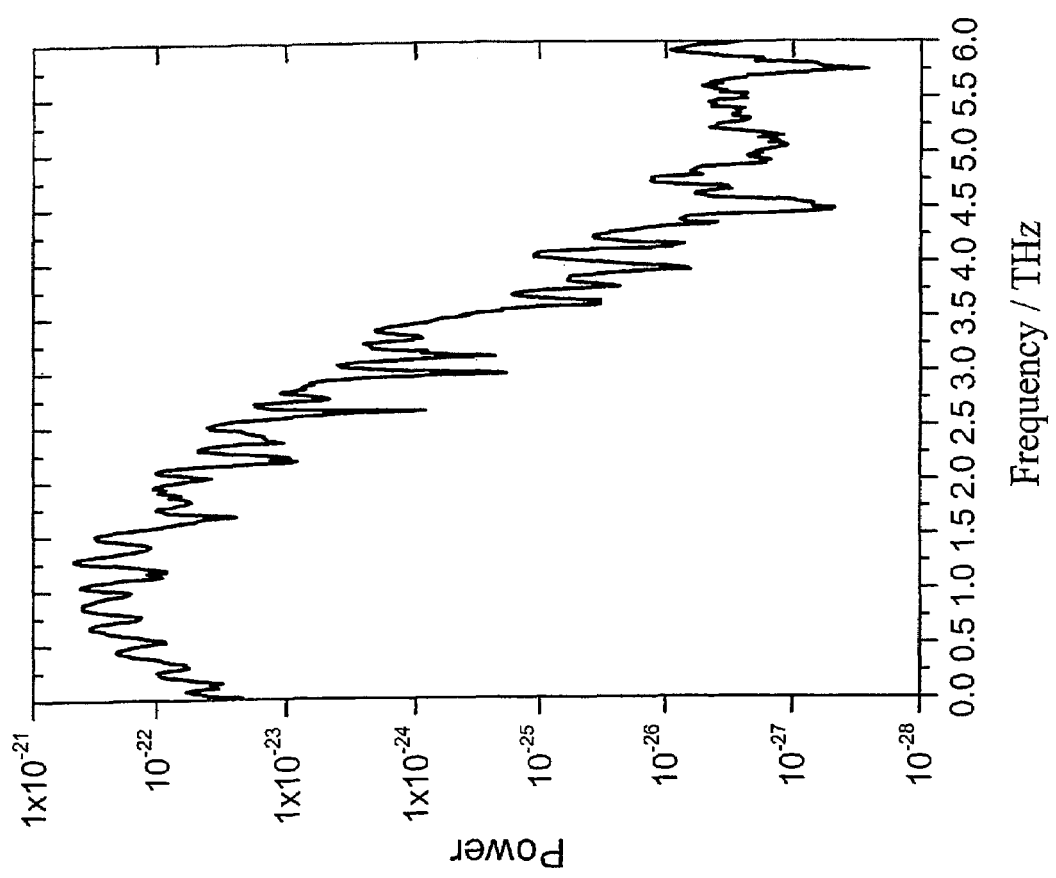
FIG. 3 illustrates a plot of detected power against frequency for a polyethylene disk.

FIG. 3 illustrates a plot of measured detected power of radiation transmitted through a sample against THz frequency for a sample comprising a polyethylene disk. The sample was performed by taking polyethylene powder and pressing it under a 2 ton weight in order to form a disk having a thickness of 1 mm.

The measurement was performed at room temperature. Polyethylene is a relatively inert material. This material is used as a reference.

Figure 4:
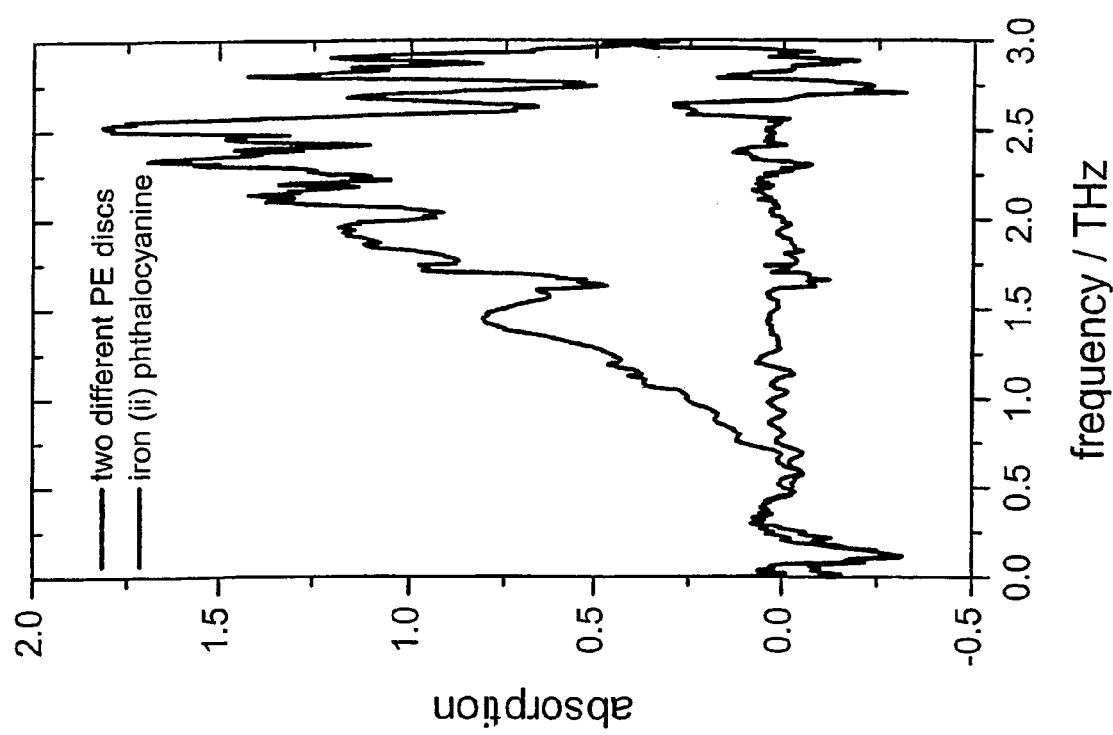
FIG. 4 illustrates both a plot of the subtracted spectra obtained from two polyethylene disks and the spectra of iron (ii) phthalocyanine and a polyethylene disk.

FIG. 4 shows two traces where absorption is plotted against frequency. Absorption is calculated from:

$$\log\left(\frac{\text{Detected radiation from sample}}{\text{Detected radiation from reference}}\right)$$

The lower trace is obtained by forming a second polyethylene disk (as described with reference to FIG. 3), obtaining the spectra of this disk and avoiding it from the spectra obtained for the first polyethylene disk (shown in FIG. 3). The log of this difference is then taken. It can be seen that this resultant trace is approximately 0.0.

The upper trace is formed by making a disk comprising a mixture of ion (ii) phthalocyanine, obtaining a spectra of this polymorphic compound and dividing the spectra with a spectra measured from one of the polyethylene disks. The divided spectra is then logged to obtain absorption which is plotted on the "y" axis.

It can be seen that the sample in the upper trace shows strong absorption characteristics, especially around 2 THz.

Ranitidine-HCl can exist in two polymorphic modifications, forms I and II, as well as in several pseudopolymorphic forms, i.e. in crystalline modifications containing solvent molecules such as ethanol or isopropanol.

Figure 5:
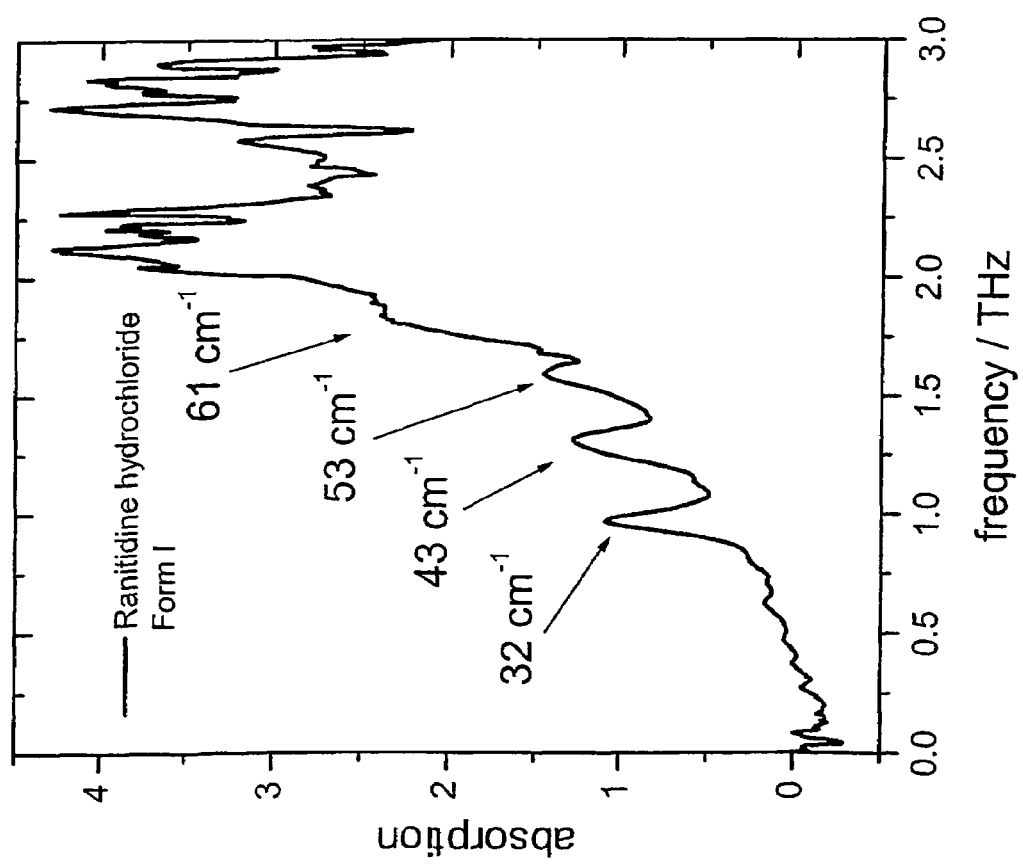
FIG. 5 illustrates a plot of a polymorph of ranitidine hydrochloride.
Figure 6:
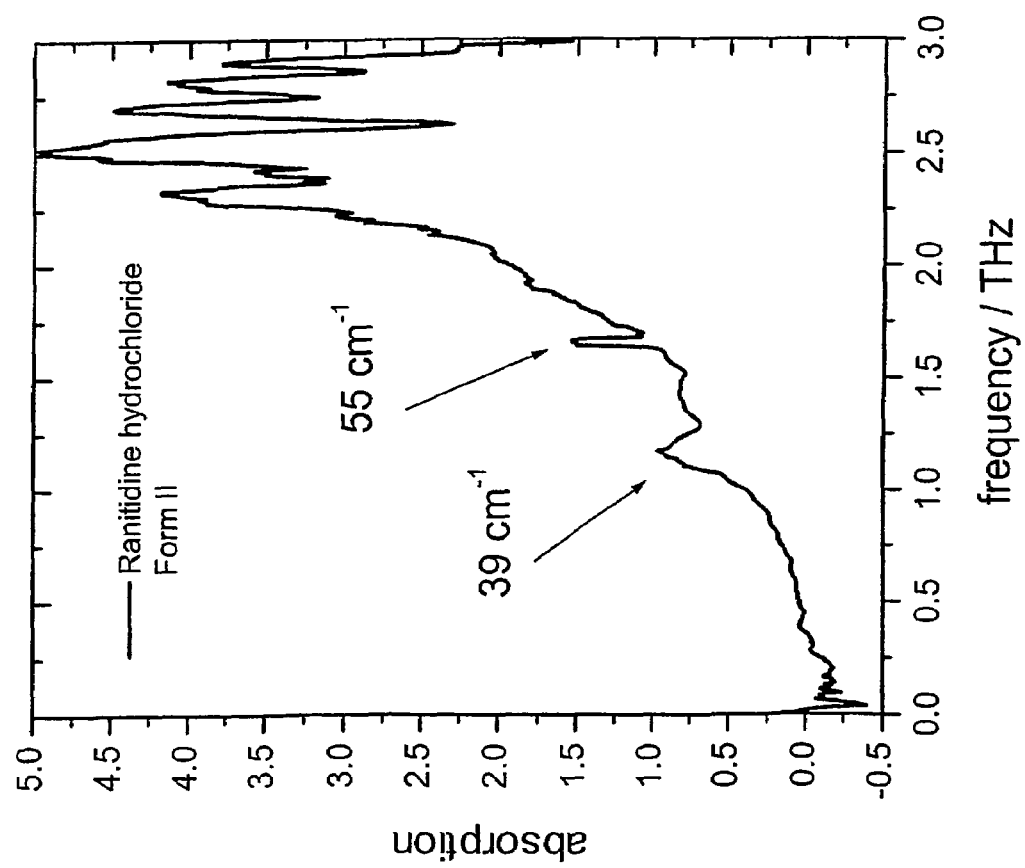
FIG. 6 illustrates a plot of a second polymorph of ranitidine hydrochloride.

FIG. 5 shows a plot of absorption coefficient against frequency for one polymorph of ranitidine hydrochloride. Ranitidine hydrochloride is often sold under the name Zantac RTM. The sample is prepared in the same way as described for ion to phthalocyanine shown in FIG. 4. FIG. 6 shows the corresponding spectra obtained for a second polymorph of ranitidine hydrochloride. Both ranitidine polymorphs are mixed with powdered polyethylene. A 50:50 by weight mixture is used.

In both of FIGS. 5 and 6, absorption is plotted against frequency. Absorption is calculated in the same manner as described for FIG. 4, where the log of the spectra obtained from the sample divided by the spectra for polyethylene is plotted.

It can be seen by comparing the spectra of FIGS. 5 and 6 that there are some remarkable differences especially in the range from 0.5 to 2 THz. The first polymorph shows strong peaks at 32 cm$^{-1}$, 43 cm$^{-1}$, 53 cm$^{-1}$ and 61 cm$^{-1}$. The second polymorph shows a strong peak at 39 cm$^{-1}$. A further peak is seen in the trace of the second polymorph at 55 cm$^{-1}$. This is believed to be due to water vapour.

Figure 7:
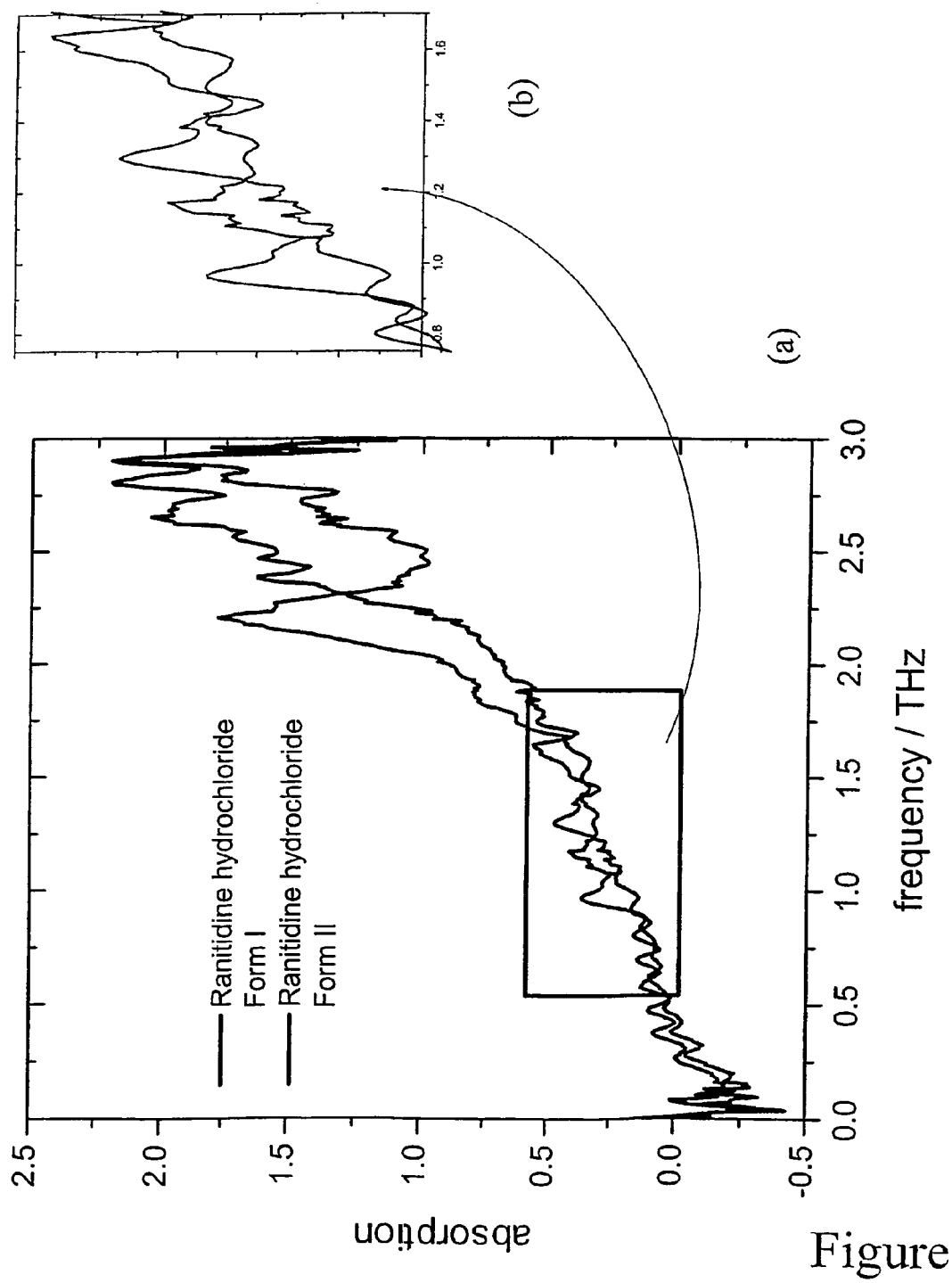
FIG. 7a illustrates a plot of absorption against THz frequencies comparing the spectra obtained from both polymorphs of ranitidine hydrochloride and FIG. 7b illustrates a detail of the region from 0.8 THz to 1.7 THz.

FIG. 7a illustrates a comparison of a further two spectra for ranitidine hydrochloride. In contrast to the samples of FIGS. 5 and 6, the samples of FIG. 7a comprise only 16% by weight of ranitidine hydrochloride as opposed to 50%.

FIG. 7b shows a detail of the region from 0.8 THz and 1.7 THz. Strong differences between the two spectra can be seen in this region. Thus, the two different polymorphs of ranitidine hydrochloride can be easily distinguished using this method. It is clear that identifying the presence of peaks which appear in the spectra of one polymorph but not in the other polymorph is much easier than trying to observe small shifts in peak position.

Figure 8:
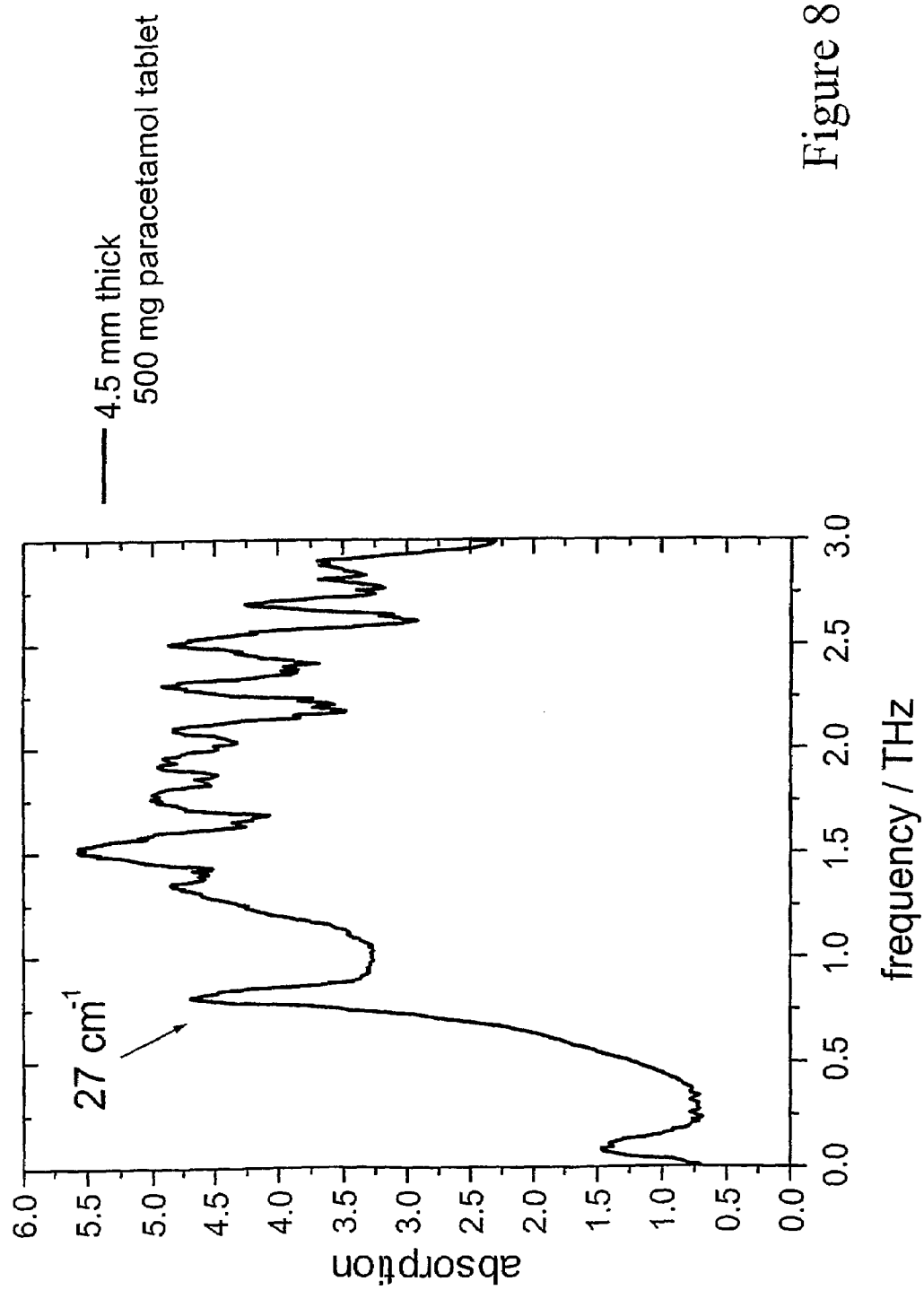
FIG. 8 illustrates the absorption of a paracetamol tablet against frequency.

FIG. 8 plots absorption against frequency for a 4.5 mm thick 500 milligram paracetamol tablet. The tablet comprises paracetamol and a further material, the composition of the inert filler material is not known.

In order to derive the absorption data, the spectra of the radiation detected from the sample is divided by a spectra of radiation detected in the absence of the sample. This "air" signal was then used as a reference and the absorption was derived in the same manner as above by plotting the log of the sample signal divided by the reference signal. It is clear from this data that the present invention can be used to analyse bulk samples.

Figure 9:
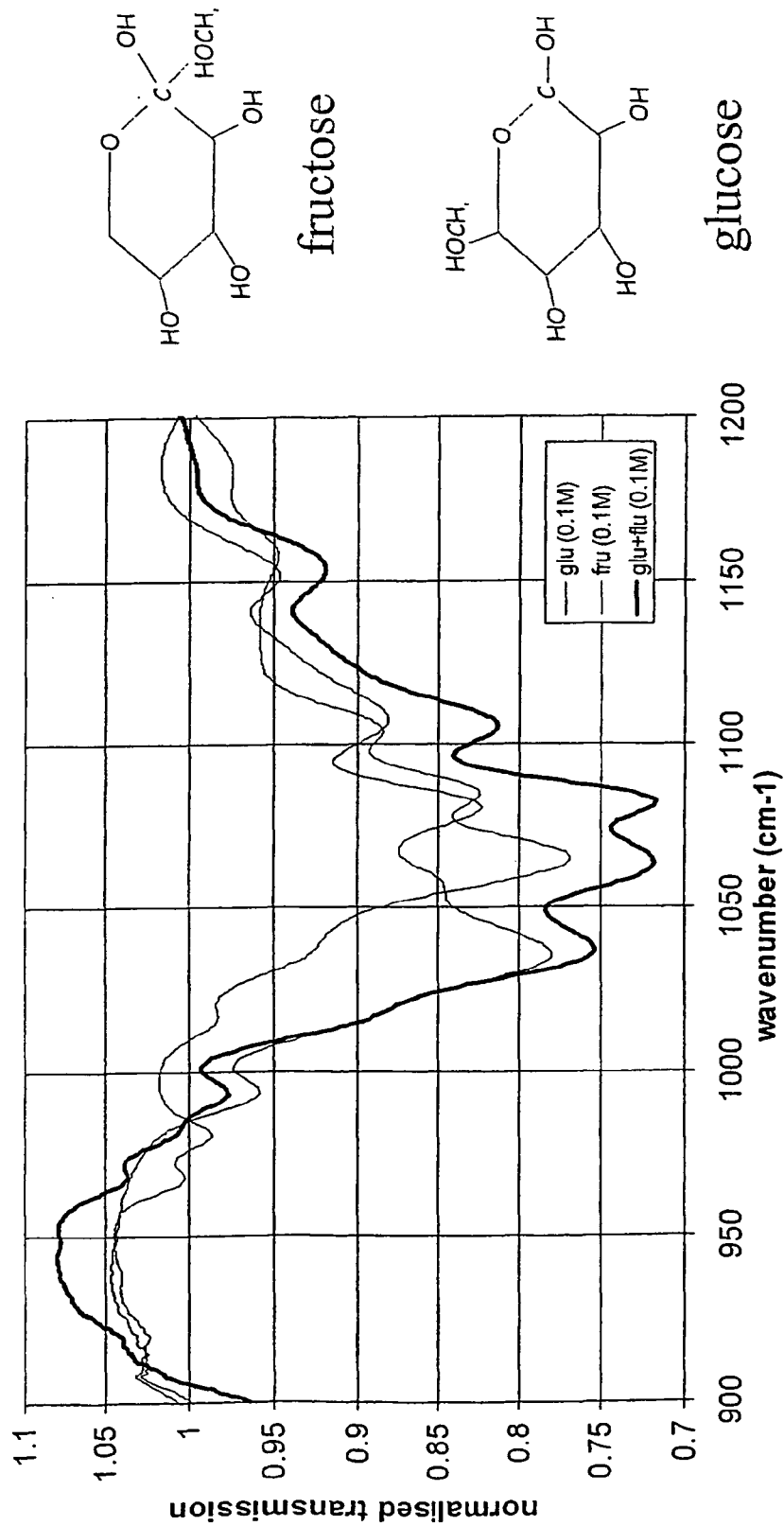
FIG. 9 illustrates a plot of transmission coefficient against wave number for fructose and glucose which are isomers.

In addition to obtaining information about the polymorphic structure of a sample, information about the intramolecular structure may be achieved by probing the sample at slightly lower frequencies. FIG. 9 illustrates the mid infra-red spectrum of glucose and fructose. Glucose and fructose are shown on the right hand side of the drawing and they can be seen to be isomers. At a wave number of 150 cm$^{-1}$, the fructose spectra is the uppermost spectra. The glucose spectra is the middle spectra and the thick spectra corresponds to a 0.1M solution of both glucose and fructose. Thus, combining this data with that in the far infra-red regime, it is possible to obtain both information concerning the polymorphic and molecular structure of a sample.

Previously, we have mainly concentrated on the use of the method to obtain information about samples in the solid phase. However, it is also possible to apply the method to samples in the liquid phase and especially samples in solution.

Figure 10:
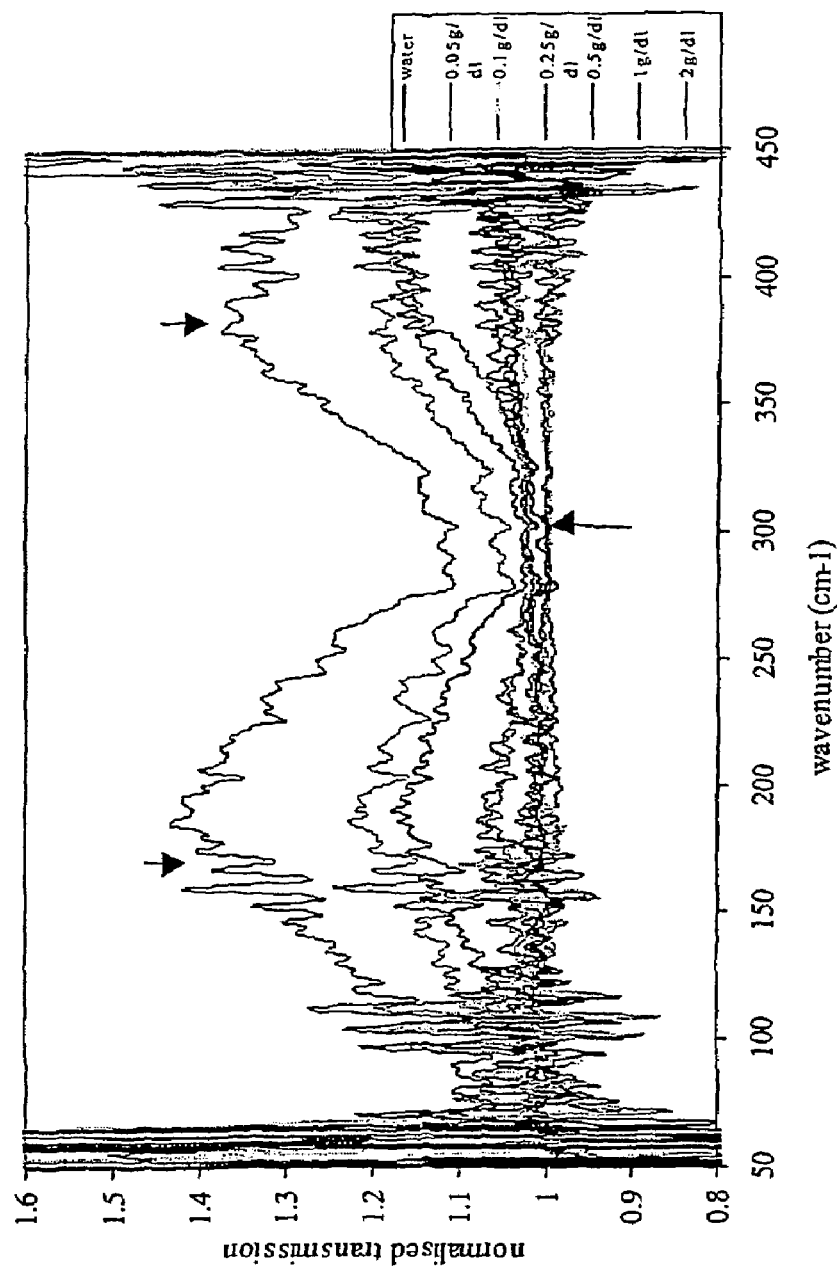
FIG. 10 illustrates a plot of transmission of radiation against wave number for a plurality of glucose solutions.

FIG. 10 illustrates the THz spectra of glucose dissolved in pure water at different concentrations. As the amount of glucose is increased from 50 mg/dl to 32 g/dl, strong absorption/bleaching features are observed in the region 2 to 9 THz (50 to 450 cm$^{-1}$). These features are due to the glucose molecule forming hydrogen bonds with nearby water molecules. Since one glucose molecule may interact with as many as eleven water molecule, bleaching of the water-water hydrogen bond vibration is noticed at 6 THz, as the glucose concentration increases.

Similarly if the experiment is repeated in an FTIR spectrometer with a sample of glucose solution dried on a piece of cellulose nitrate filter paper, the absorption of THz radiation increases at 9 THz. This absorption band is due to the hydrogen-bonded vibration between with water and glucose molecules. In this experiment all the non-hydrogen bonded water was removed, leaving only water that has been hydrogen bonded with the glucose molecule thus revealing a strong absorption peak at 9 THz.

FIG. 11a illustrates absorption spectra for different samples of the two polymorphs of ranitidine HCl as described in relation to FIGS. 5 and 6. FIG. 11b highlights the region around 1.1 THz where there are considerable changes in the spectra between the two polymorphs.

The table below illustrates the position of the peaks in THz recorded for the first and second polymorphs of FIGS. 11a and 11b. This data was obtained by fitting the peaks to a series of Lorentzian lineshape functions.

| First Polymorph | Second Polymorph |
| --- | --- |
| 2.76 | 2.76 |
| 2.55 | 2.39 |
| 2.20 | 2.26 |
| 2.04 | 1.85 |
| 1.78 | 1.40 |
| 1.53 | 1.13 |
| 1.26 | |
| 0.95 | |

FIG. 12a is a plot of the absorption spectra for the drug Zantac. FIG. 12b is a plot of the refractive index against frequency for the drug Zantac. FIG. 13a is a plot of the absorption spectra for the drug Apo-ranitidine. FIG. 13b is a plot of the refractive index against frequency for the drug Apo-ranitidine. By comparing the spectra of FIG. 11a with that of FIGS. 12a and 13a, it is clear that Zantac is based on the second polymorph and Apo-ranitidine contains the first polymorph.

FIGS. 14a to 14d are spectra for four ranitidine drug dosage tablets at room temperature from the following manufacturers (a) Eastern Pharmaceuticals Ltd., (b) Generics UK Ltd., (c) Tillomed and (d) Norton Ranbaxy Laboratories. It can be seen from comparison with FIG. 11a that they all contain the first polymorph.

The invention claimed is:

1. A method for investigating the macro structure of a sample, the method comprising:
   irradiating the sample with radiation having a plurality of frequencies in the range from 25 GHz to 20 THz;
   detecting radiation reflected from and/or transmitted by said sample to obtain a spectra of the sample; and
   identifying structure in the resultant spectra which arises from intermolecular interactions in order to determine information about the macrostructure of the sample.

2. A method according to claim 1, further comprising irradiating the sample with radiation in the range of 25 THz to 120 THz and identifying structure in the resultant spectra which arises from intramolecular vibrations.

3. A method according to either of claims 1 or 2, wherein the radiation is pulsed radiation.

4. A method according to claim 3, further comprising the step of deriving the refractive index of the sample.

5. A method according to claim 3, wherein said sample is held at a maximum temperature of up to 150K during irradiation.

6. A method according to claim 5, wherein said sample is held at a maximum temperature of up to 101K.

7. A method according to claim 3, wherein the sample is under vacuum when irradiated.

8. A method according to claim 3, wherein the sample is under dry nitrogen or dry air when irradiated.

9. A method according to claim 3, wherein the sample is powderized and mixed with an inert material prior to irradiation.

10. A method according to claim 9, wherein the inert material is polyethylene.

11. A method according to claim 3, wherein said sample is at most 5 mm thick.

12. A method according to claim 3, adapted for assessing samples after storage, where the resultant spectra is compared with the known spectra of the molecule.

13. A method according to claim 3, wherein the sample is irradiated while located in a plastic bag.

14. A method according to claim 3, wherein the step of identifying structure in the resultant spectra comprises comparing the resultant spectra with known spectra.

15. A method as claimed in claim 1, wherein the step of identifying the structure in the resultant spectra comprises determining information concerning the polymorphic structure of the sample.

16. A method according to either of claims 1 or 2, wherein the radiation is continuous wave radiation.

17. A method according to claim 16, further comprising the step of deriving the refractive index of the sample.

18. A method according to claim 16, wherein said sample is held at a maximum temperature of up to 150K during irradiation.

19. A method according to claim 18, wherein said sample is held at a maximum temperature of up to 101K.

20. A method according to claim 16, wherein the sample is under vacuum when irradiated.

21. A method according to any of claim 16, wherein the sample is under dry nitrogen or dry air when irradiated.

22. A method according to claim 16, wherein the sample is powderized and mixed with an inert material prior to irradiation.

23. A method according to claim 22, wherein the inert material is polyethylene.

24. A method according to claim 16, wherein said sample is at most 5 mm thick.

25. A method according to claim 16, adapted for assessing samples after storage, where the resultant spectra is compared with the known spectra of the molecule.

26. A method according to claim 16, wherein the sample is irradiated while located in a plastic bag.

27. A method according to claim 16, wherein the step of identifying structure in the resultant spectra comprises comparing the resultant spectra with known spectra.

28. method according to either of claims 1 or 2, further comprising the step of deriving the refractive index of the sample.

29. A method according to claims 1 or 2, wherein said sample is held at a maximum temperature of up to 150K during irradiation.

30. A method according to claim 29, wherein said sample is held at a maximum temperature of up to 101K.

31. A method according to either of claims 1 or 2, wherein the sample is under vacuum when irradiated.

32. A method according to either of claims 1 or 2, wherein the sample is under dry nitrogen or dry air when irradiated.

33. A method according to either of claims 1 or 2, wherein the sample is powderized and mixed with an inert material prior to irradiation.

34. A method according to claim 33, wherein the inert material is polyethylene.

35. A method according to either of claims 1 or 2, wherein said sample is at most 5 mm thick.

36. A method according to either of claims 1 or 3 adapted for quality control, where the resultant spectra is compared with the known spectra of the molecule.

37. A method according to either of claims 1 or 2, adapted for assessing samples after storage, where the resultant spectra is compared with the known spectra of the molecule.

38. A method according to either of claims 1 or 2, wherein the sample is irradiated while located in a plastic bag.

39. A method according to either of claims 1 or 2, wherein the step of identifying structure in the resultant spectra comprises comparing the resultant spectra with known spectra.

40. An apparatus for studying the macro structure of a molecular sample, the apparatus comprising:
    an emitter for irradiating the sample with radiation having a plurality of frequencies in the range from 25 GHz to 20 THz;
    a detector for detecting radiation reflected from and/or transmitted by the sample and producing a spectra of the sample; and
    means for identifying structure in the spectra arising from intermolecular interactions in order to determine information about the macrostructure of the sample.

41. An apparatus according to claim 40, wherein said means for identifying structure comprises means to compare the detected spectra with known spectra.

42. An apparatus according to claim 41, configured to monitor quality of a batch of samples, said apparatus comprising means to set a known spectra of the desired Polymorph and means to compare spectra produced from each of said samples with said known spectra.

* * * * *